United States Patent
Victor et al.

(10) Patent No.: US 10,274,021 B2
(45) Date of Patent: Apr. 30, 2019

(54) TWO STAGE TORQUE LIMITER

(71) Applicant: Greatbatch Ltd., Clarence, NY (US)

(72) Inventors: Gary C. Victor, Wheatfield, NY (US); Neal N. Nesselbeck, Lockport, NY (US)

(73) Assignee: VIANT AS&O HOLDING, LLC, Tempe, AZ (US)

( * ) Notice: Subject to any disclaimer, the term of this patent is extended or adjusted under 35 U.S.C. 154(b) by 406 days.

(21) Appl. No.: 15/131,167

(22) Filed: Apr. 18, 2016

(65) Prior Publication Data

US 2016/0305497 A1    Oct. 20, 2016

Related U.S. Application Data

(60) Provisional application No. 62/148,766, filed on Apr. 17, 2015.

(51) Int. Cl.
*F16D 7/02* (2006.01)
*F16D 9/06* (2006.01)
(Continued)

(52) U.S. Cl.
CPC ............. *F16D 7/024* (2013.01); *A61B 17/16* (2013.01); *A61B 17/1624* (2013.01);
(Continued)

(58) Field of Classification Search
CPC . A61B 17/16; A61B 17/1615; A61B 17/1624; A61B 17/1628; A61B 17/164;
(Continued)

(56) References Cited

U.S. PATENT DOCUMENTS

| 406,374 A | 7/1889 | Steward |
| 2,333,553 A * | 11/1943 | Potgieter ................ F16D 7/044 464/38 |

(Continued)

FOREIGN PATENT DOCUMENTS

| DE | 2056755 A1 * | 6/1971 | ............. F16D 7/044 |
| JP | 2001121444 | 5/2001 | |
| WO | 2005014232 | 2/2005 | |

OTHER PUBLICATIONS

Extended European Search, Application 16165826.5, dated Oct. 6, 2016.

*Primary Examiner* — Josh Skroupa
(74) *Attorney, Agent, or Firm* — Grossman, Tucker, Perreault & Pfleger, PLLC

(57) ABSTRACT

A torque limiting tool comprises a two stage torque limiting mechanism that resides within a housing. The torque limiting mechanism comprises a shank positioned through a gear, a plate, and a bias member. The plate is constructed having at least one post and at least one tooth providing a ramp surface that extends outwardly from a plate surface. The gear is constructed having at least one recess providing at least one inclined surface that resides part-way within the thickness of the gear. The gear and plate are positioned in opposition so that the at least one tooth and extending post are received within or detachably mated to the opposing recess and through-bore. Torque is transferred therebetween the plate and gear when the ramped teeth and extending posts mate with the respective recess and through-bore. A first torque limit is exceeded when the post breaks free from the through-bore. A second, lesser torque limit is exceeded when the ramped teeth release from their mated recess.

35 Claims, 10 Drawing Sheets

(51) Int. Cl.
*F16D 43/21* (2006.01)
*A61B 17/16* (2006.01)
*B25F 5/00* (2006.01)
*A61B 17/88* (2006.01)
*A61B 90/00* (2016.01)

(52) U.S. Cl.
CPC ............... *B25F 5/001* (2013.01); *F16D 9/06* (2013.01); *F16D 43/215* (2013.01); *A61B 17/164* (2013.01); *A61B 17/8875* (2013.01); *A61B 2090/031* (2016.02)

(58) Field of Classification Search
CPC ............... A61B 17/80; A61B 17/8875; A61B 2090/031; F16D 7/024; F16D 7/042; F16D 7/044; F16D 7/046; F16D 9/06; F16D 43/2022; F16D 43/2024; F16D 43/2026; F16D 43/213; F16D 43/215
USPC ......... 464/30, 38, 39; 192/54.5; 173/5, 93.5, 173/178; 81/467, 473–476
See application file for complete search history.

(56) References Cited

U.S. PATENT DOCUMENTS

| | | | |
|---|---|---|---|
| 3,613,751 A * | 10/1971 | Juhasz | B25B 21/00 81/474 |
| 3,695,059 A | 10/1972 | Laubach | |
| 4,063,474 A | 12/1977 | Klopping | |
| 4,545,470 A * | 10/1985 | Grimm | F16D 43/213 188/134 |
| 4,569,250 A * | 2/1986 | Nellums | F16D 43/216 192/54.5 |
| 5,746,298 A | 5/1998 | Krivec et al. | |
| 6,132,435 A * | 10/2000 | Young | A61B 17/8875 192/56.54 |
| 6,487,943 B1 | 12/2002 | Jansson et al. | |
| 7,025,151 B2 | 4/2006 | Hehli et al. | |
| 7,127,955 B2 | 10/2006 | Bondhus et al. | |
| 7,197,968 B2 | 4/2007 | Bubel | |
| 7,334,509 B1 | 2/2008 | Gao | |
| 7,475,619 B2 | 1/2009 | Chiu et al. | |
| 7,762,164 B2 | 7/2010 | Nino et al. | |
| 7,938,046 B2 | 5/2011 | Nino et al. | |
| 8,549,963 B2 | 10/2013 | Chuang | |
| 8,757,035 B2 | 6/2014 | Kerboul et al. | |
| 8,833,211 B2 | 9/2014 | Chuang | |
| 2002/0100346 A1 | 8/2002 | Binns | |
| 2007/0006692 A1 | 1/2007 | Phan et al. | |
| 2010/0275746 A1 | 11/2010 | Wengreen | |
| 2011/0017801 A1 | 1/2011 | Zemlok et al. | |
| 2013/0152746 A1 | 6/2013 | Kerboul et al. | |
| 2014/0155900 A1 | 6/2014 | Giersch et al. | |
| 2014/0171989 A1 | 6/2014 | Robinson et al. | |
| 2014/0366691 A1 | 12/2014 | Ivinson et al. | |
| 2014/0373691 A1 | 12/2014 | Tien-Lung | |

\* cited by examiner

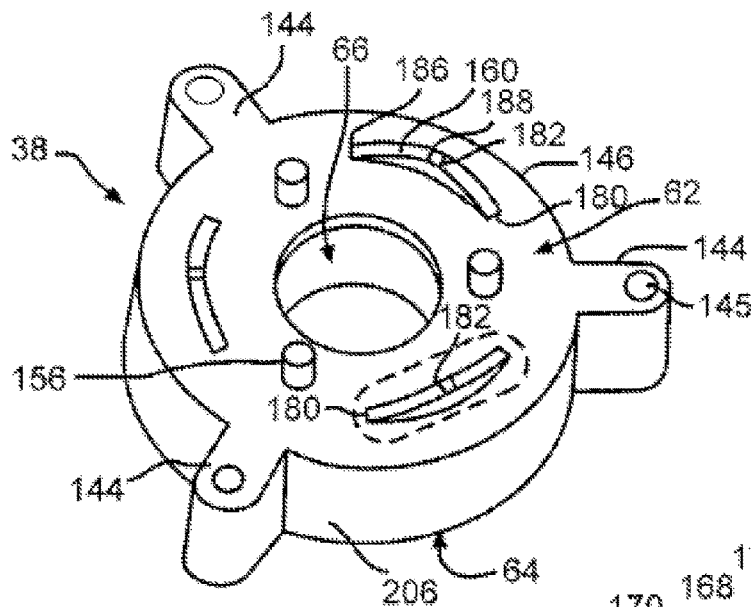
FIG. 4
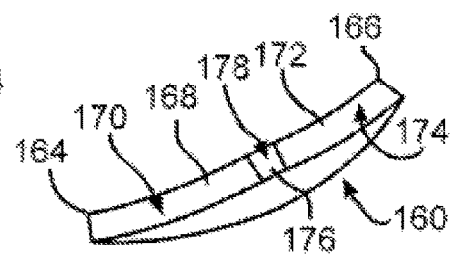
FIG. 4A
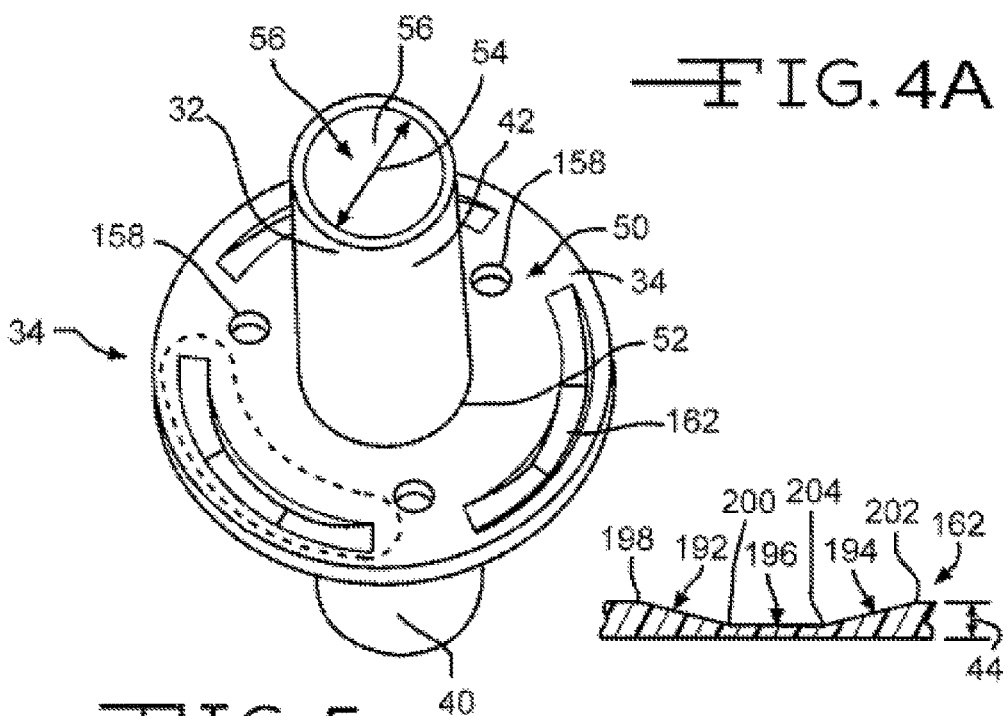
FIG. 5
FIG. 5A

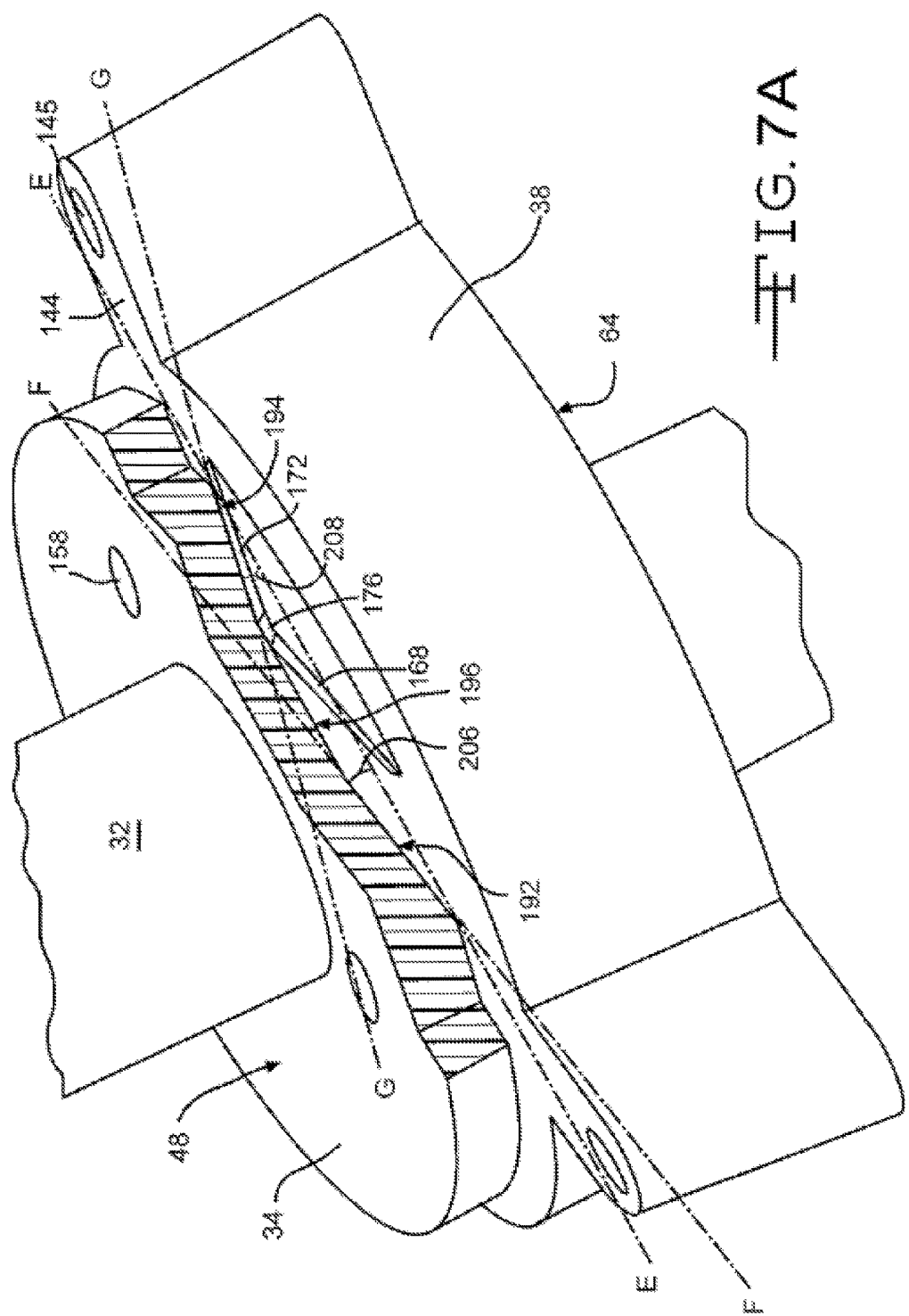

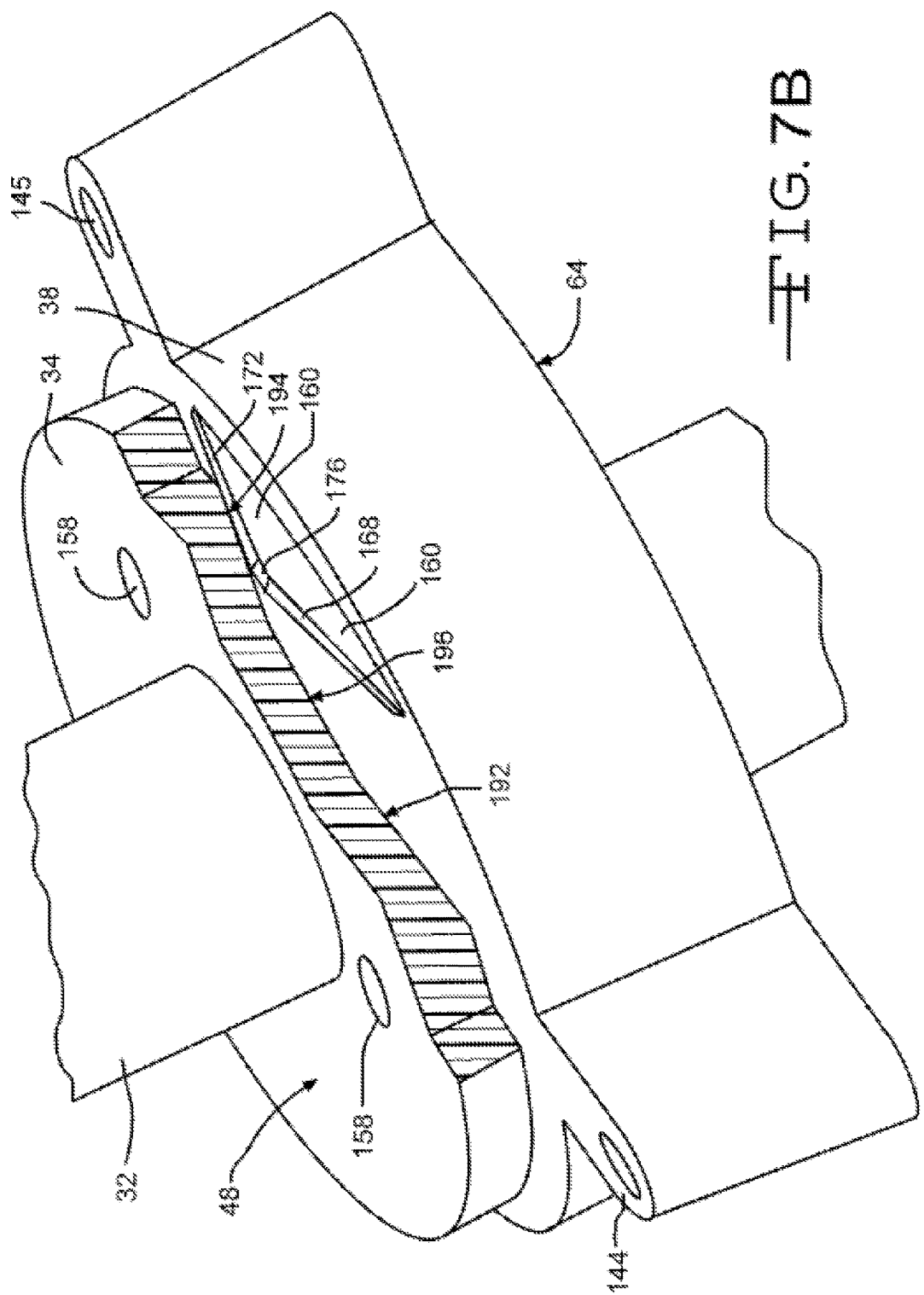

ically, the torque limiting tool of the present invention is configured to modify the maximum amount of torque that is capable of being applied after a first pre-determined torque limit has been exceeded. The torque limit of the present invention can be used to tighten a fastener, such as a fastener used to secure an orthopedic implant or bone plate, or alternatively, it may be used to limit the amount of torque that is applied during an orthopedic surgical reaming procedure.

TWO STAGE TORQUE LIMITER

CROSS REFERENCE TO RELATED APPLICATION

This application claims priority from U.S. Provisional Application Ser. No. 62/148,766, filed Apr. 17, 2015.

TECHNICAL FIELD

This invention relates to the art of instruments used in orthopedic surgical procedures. More specifically, this invention relates to a torque limiting tool that is used to limit the amount of torque that is applied during an orthopedic surgical reaming procedure.

BACKGROUND OF THE INVENTION

Torque limiting tools are widely used to tighten a fastener to a specific torque. Such tools are extensively used during surgical procedures, such as an orthopedic surgical procedure. For example, a torque limiting tool may be used to tighten a fastener that is used to secure an orthopedic implant or bone plate. As such, it is often important that the fastener is tightened to a specific torque. Over-tightening a fastener could result in damage to the orthopedic implant or bone plate. Likewise, a fastener that is not adequately tightened may result in undesirable movement of the implant or bone plate within the patient. Such movement of the orthopedic implant or bone plate may be adverse to a patient as the implant may move to a position that does not allow proper bone repair.

In addition, torque limiting tools may also be used to control the amount of torque that is applied during an orthopedic surgical procedure, such as the reaming of a bone. One such procedure is the reaming of the intramedullary canal of a long bone, such as a femur. During the procedure, a cutting tool that is positioned at the end of a shaft is inserted within the intramedullary canal. Torque applied to the shaft rotates the cutting tool so that tissue and bone material are removed from the canal. It is important that an appropriate amount of torque is applied to the shaft during this reaming procedure to ensure that the canal is appropriately reamed. Application of an excessive amount of torque however, may adversely result in damage to the shaft or the canal. Therefore, it is important that the amount of applied torque is limited to minimize the possibility of causing injury to the patient.

In some instances during an orthopedic reaming procedure, such as the reaming of the intramedullary canal, an obstacle may be encountered that causes the cutting tool to become immobilized therewithin. When a cutting tool becomes immobilized, continued application of torque may cause the shaft to fracture within the canal, which may result in injury to the patient. Furthermore, extraction of an immobilized cutting tool is particularly problematic as it may become necessary to further limit the amount of torque applied to the shaft to minimize potential damage to the patient. Therefore, a torque limiting tool is needed that applies torque to the shaft in two stages; one stage, having a first torque limit to allow application of an appropriate amount of torque to effectively ream a bone; and, a second stage, having a second torque limit that is different than the first torque limit that allows for the safe removal of the tool. More specifically, a tool is needed that is capable of providing a first maximum amount of torque during a first stage in which a bone is being reamed, and, in addition, is capable of limiting the application of torque to a second maximum torque amount that is less than the first maximum torque amount so that removal of the shaft and cutting tool is enabled.

The present invention provides a torque limiting tool having a mechanism that limits the application of torque at two separate stages. The tool of the present invention is designed so that application of torque in excess of a first pre-determined maximum torque threshold causes the mechanism to be modified so that further application of torque is limited to a second maximum torque threshold of a lesser amount. In contrast, most prior art torque limiting tools typically prevent the application of torque up to a single maximum torque limit and do not have the capability of limiting torque at different threshold amounts, such as at two different stages with the same mechanism.

For example, in the case of reaming an intramedullary canal, the first stage provides for the application of a first maximum amount of torque that allows for optimal removal of material therewithin. However, in the event that the reaming tool should become immobilized in, for example, the intramedullary canal, the torque limiting device of the present invention is designed to operate at a second stage in which the application of torque is limited to a second, lower torque threshold amount thereby minimizing potential bone damage during removal of the cutting tool.

SUMMARY OF THE INVENTION

The present invention provides a torque limiting tool and mechanism thereof that is designed to limit the application of torque at two different threshold amounts. More specifi The tool of the present invention comprises a two-stage torque limiting mechanism that resides within the housing of the tool. The mechanism comprises a shank secured to a gear that is releasably mated to a plate. A bias member provides a bias force that encourages mating of the gear and plate. Torque is transferred from the housing to a connectable drive shaft when the gear and plate are in a mated relationship.

In an embodiment, the plate comprises at least one tooth having at least one ramp surface that outwardly extends from the plate surface. In addition, at least one post extends from the exterior plate surface. The raised tooth of the plate is positioned in opposition to a corresponding recess that resides at least partially within the thickness of the gear positioned opposed to the plate. The outwardly extending post is received in a corresponding through-bore or opening that extends at least partially through the thickness of the opposing gear. The bias member is positioned about the shank of the gear and provides a biasing force against the gear that enhances the engagement of the teeth and post within the recess and through-bore of the gear, respectively.

Torque is transferred in a first stage configuration when the at least one post and tooth are engaged within their respective recess and through-bore. When the torque limiting mechanism is in this first stage configuration, a torque of up to a first torque limit is capable of being applied by the mechanism and tool. Continued application of torque in excess of this first torque limit threshold causes the at least one post to become disengaged from within its corresponding through-bore. It is at this point when the at least one post becomes disengaged from its corresponding through-bore or opening, that the mechanism becomes configured in a second stage in which the amount of torque that is capable of being applied is limited to a second torque threshold that is different than the first. In a preferred embodiment, the second torque threshold of the second configuration is less than the first threshold amount of the first configuration.

In a preferred embodiment, the proximal end of the housing comprises a keyed driver end. This keyed driver end is designed to engage with a motor or another device that imparts rotational movement to the housing. Torque that is applied to the keyed driver end at the proximal end of the housing is transferred to the plate that is physically connected at the distal end of the housing. Torque generated from rotation of the plate is thus transferred to the gear that is positioned in a mated relationship with the plate. The torque that is transferred to the gear, in turn, is transferred to a drive shaft that is connected to the gear. Likewise, when the gear is disengaged from the plate, torque is not transferred from the keyed driver end of the housing to the drive shaft.

Furthermore, the amount of torque imparted by the tool in either the first or second stage configuration is established by either of the post or respective ramped teeth surfaces to resist mechanical flexure. This is influenced by the combination of the diameter thickness of the post, the angle of the ramped surfaces of the respective tooth and recess, the strength of the bias force exerted by the biasing member and the material composition of the gear and plate. The angle of the ramped surfaces of the mated teeth and recess establish the point of contact and influence the amount of friction between the gear and plate. In addition, the strength of the bias force exerted by the biasing member against the gear also influences the amount of friction between the opposing gear and plate. Thus, the amount of force, i.e., torque, required to break the post and deflect the ramped surface of the ridge against the trough surface can be modified.

In addition, the amount of torque imparted by the tool is influenced by the material of which the gear and plate are constructed. Material selection can have a direct effect on the flexural movement of the post and/or the ramped surface of the ridge as different materials have differing mechanical properties. For example, materials having an increased modulus of elasticity tend to exhibit a greater mechanical stiffness, thereby requiring the application of a greater force to bend or flex the material. Therefore, constructing the gear and plate of a material having a greater modulus of elasticity requires the application of an increased amount of force to flex and separate the respective gear and plate, thus increasing the amount of torque imparted by the tool. These and other additional unique structural features of the torque limiting tool will be discussed in further detail.

BRIEF DESCRIPTION OF THE DRAWINGS

FIG. 4 is a magnified view of a plate component that is comprised within the torque limiting mechanism of the present invention.

FIG. 4A is a magnified view of an embodiment of a tooth outwardly extending from the plate shown in FIG. 4.

FIG. 5 is a magnified view of an embodiment of a shank extending through a gear that is configured within the torque limiting mechanism of the present invention.

FIG. 5A illustrates a magnified view of a recess that at least partially extends within the thickness of the gear.

FIGS. 7A-7C are magnified partially broken perspective views that illustrate the relationship of the plate and gear as a torque is applied in a clockwise direction.

DETAILED DESCRIPTION OF THE PREFERRED EMBODIMENT

Figure 1:
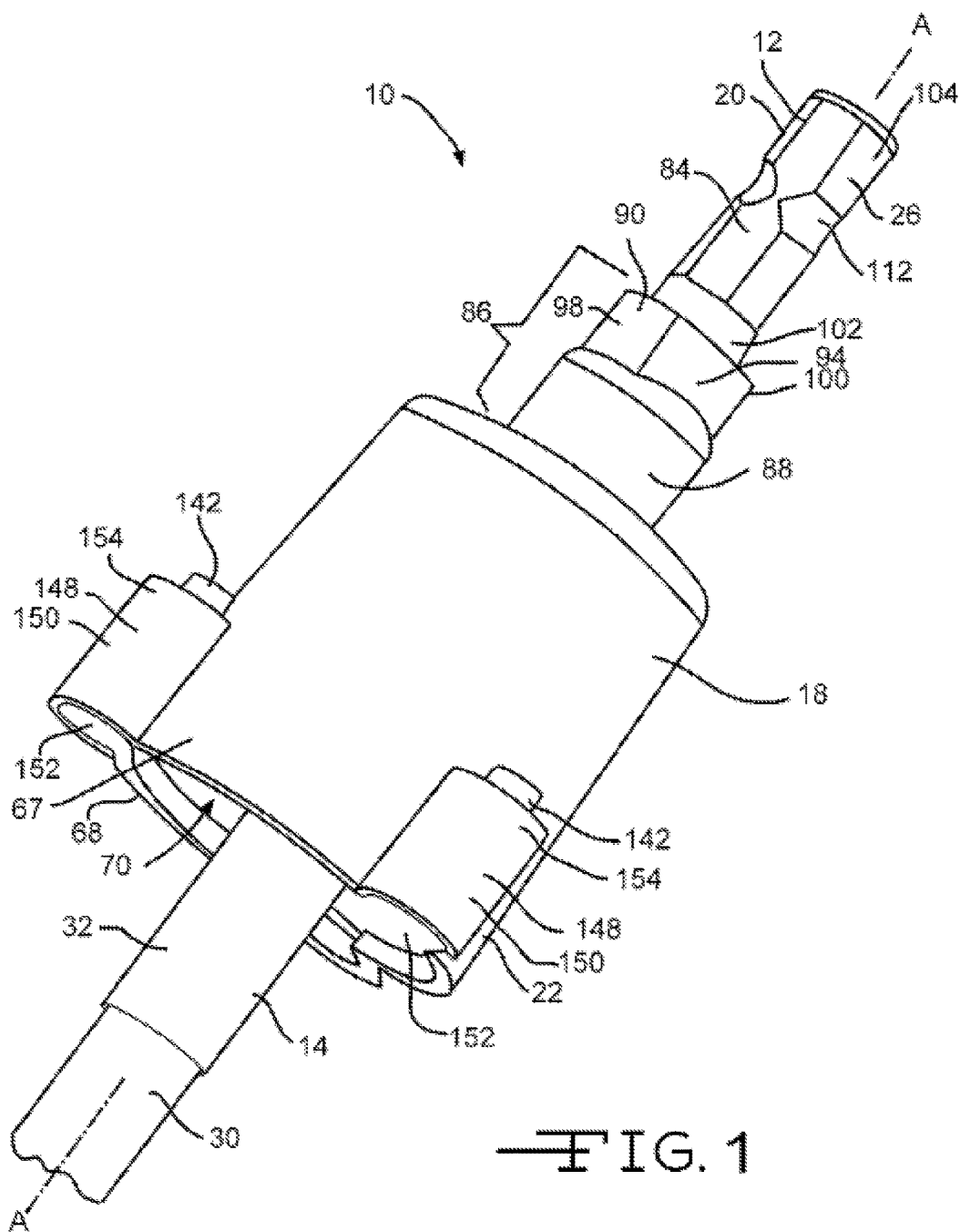
FIG. 1 illustrates a perspective view of an embodiment of the torque limiting tool of the present invention.
Figure 1A:
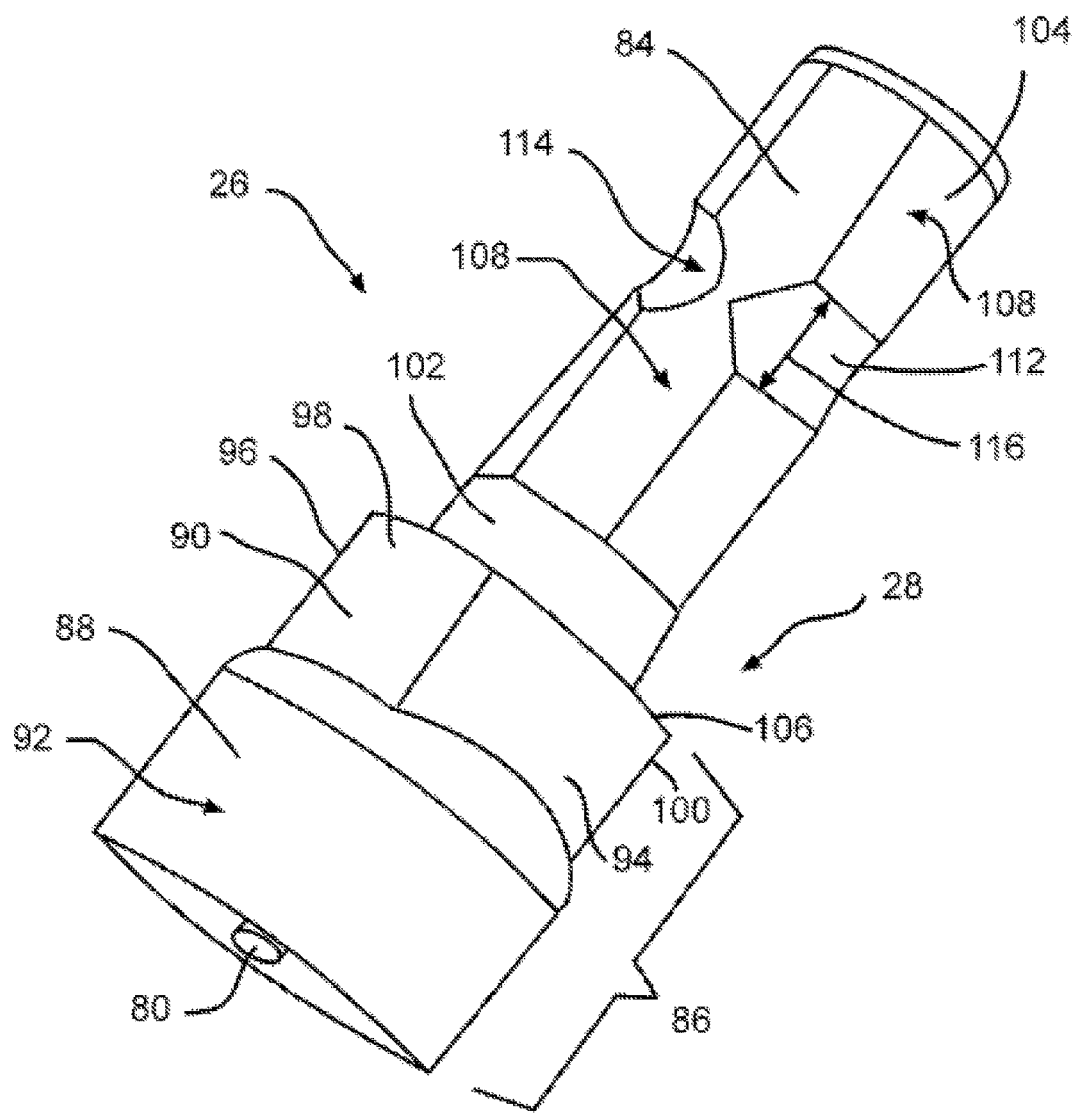
FIG. 1A illustrates a magnified view of an embodiment of a driver end of the torque limiting tool of the present invention.
Figure 2:
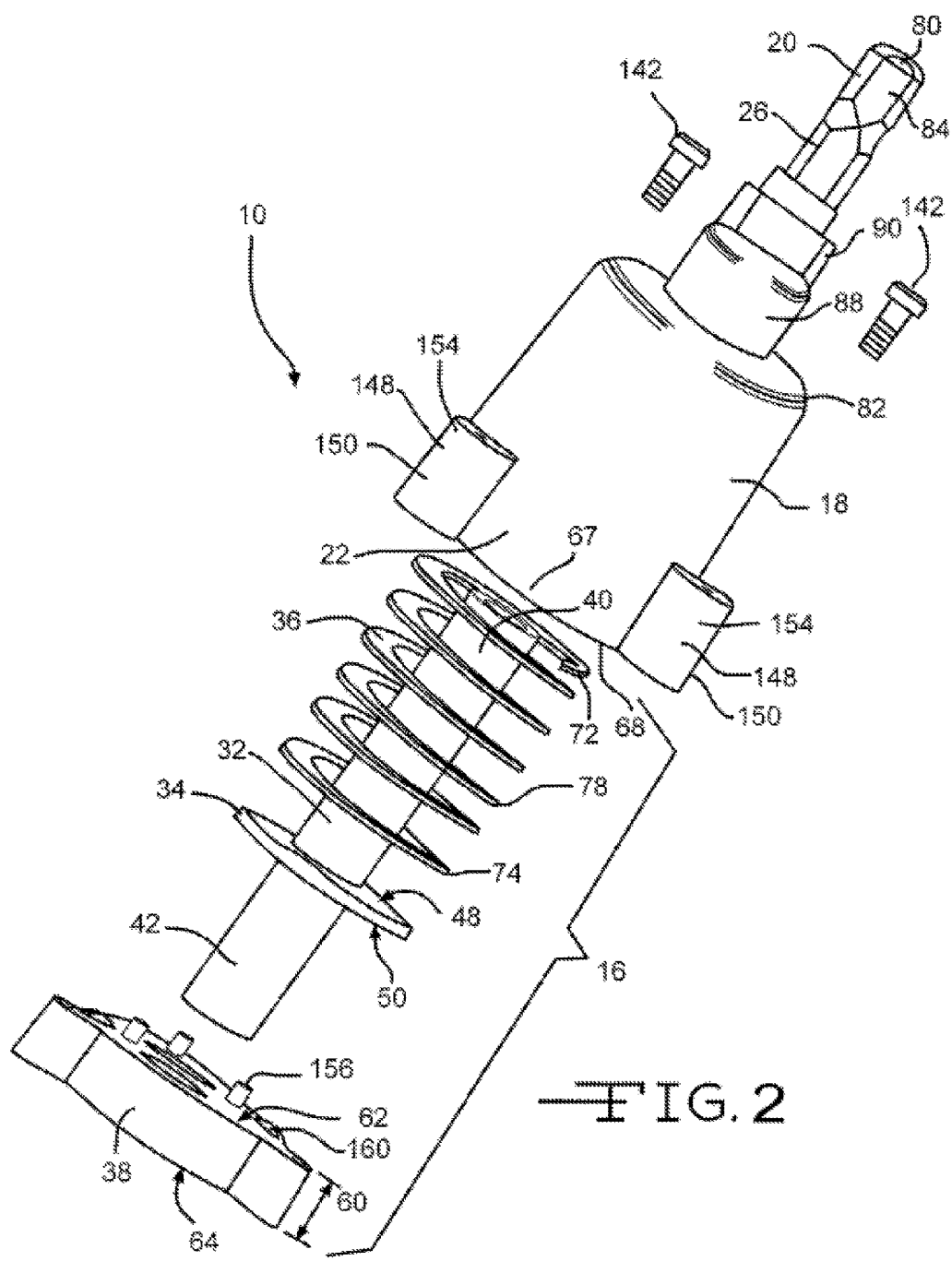
FIG. 2 shows an exploded view of an embodiment of the components that comprise the torque limiting tool of the present invention shown in FIG. 1.
Figure 3:
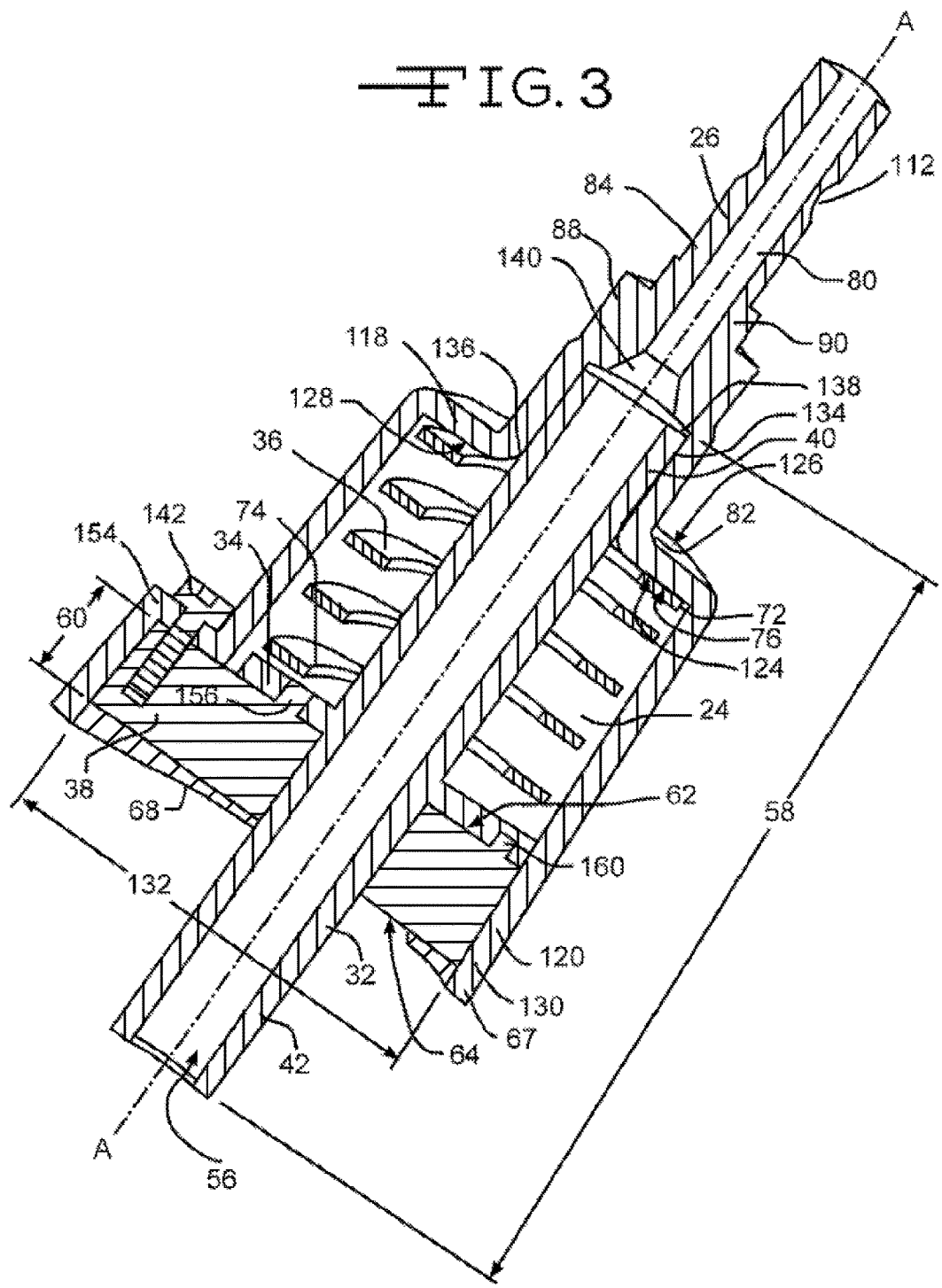
FIG. 3 is a cross-sectional view taken along longitudinal axis A-A of the embodiment of the torque limiting tool shown in FIG. 1.

Now turning to the figures, FIGS. 1, 2, and 3 illustrate a preferred embodiment of a two-stage torque limiting tool 10 of the present invention. As shown, the tool 10 extends along longitudinal axis A-A from a proximal end 12 to a distal end 14. In an embodiment, the tool 10 comprises a torque limiting mechanism 16 (FIG. 2) that resides within a housing 18 having a proximal housing portion 20 that extends to a distal housing portion 22. The torque limiting mechanism 16 is preferably positioned within an interior 24 of the distal portion 22 of the housing 18. As illustrated, the distal housing portion 22 comprises a driver end 26 having a keyed interface 28 (FIG. 1A). The keyed driver end 26 is designed to engage with a device or motor (not shown) that enables the housing 18 to be rotated in either a clockwise or counterclockwise direction about longitudinal axis A-A which acts as the rotational axis of the tool 10.

The torque limiting tool 10 of the present invention is designed to transfer a torque applied at the driver end 26 of the proximal housing portion 20 to a drive shaft 30 that is connectable to a shank 32 of the torque limiting mechanism 16. In a preferred embodiment, the mechanism 16 of the present invention is a two-stage torque limiting mechanism. This means that the torque limiting mechanism of the present invention is configured to limit the application of torque up to a second torque threshold of a lesser magnitude after a first threshold of a greater magnitude of torque has been applied to the drive shaft 30. The mechanism 16 of the present invention is constructed so that once a torque exceeding a first torque threshold is applied to the drive shaft 30, the applied torque causes the mechanism 16 to be physically modified so that the mechanism's ability to apply torque is limited to a second threshold of a lesser magnitude. Thus, the torque limiting mechanism 16 of the present invention is a two-stage mechanism in that the application of torque by the mechanism is limited up to a second lesser torque amount once a torque exceeding a first torque amount has occurred.

As defined herein, torque is a twisting force that tends to cause rotation. More specifically, torque is a measure of a force's tendency to produce rotation about an axis that is equal to the product of the force vector and the radius vector from the axis of rotation to the point of application of the force. Torque has dimensions of force times distance. The International System of Units or SI unit for torque is the Newton meter (Nm). Other non-SI units of torque include pound-force-feet, foot-pounds-force, meter-kilograms-force, inch-ounces, and inch-pounds.

FIG. 2 illustrates an exploded view of the torque limiting tool 10 of the present invention and mechanism 16 thereof. As shown, the torque limiting mechanism 16 comprises a gear 34, a biasing member 36, and a plate 38. In a preferred embodiment, the gear 34 is a disc-shaped member constructed with the shank 32 extending through its thickness 44 (FIGS. 5, 5A). As shown, the proximal and distal ends 40, 42 of the shank 32 outwardly extend from opposed first and second gear surfaces 48, 50. In a preferred embodiment, the shank 32 is fixedly positioned within the gear thickness 44 so that the first and second gear surfaces 48, 50 are oriented about perpendicular to the length of the shank 32.

As illustrated in FIG. 5, the shank 32 is preferably positioned along longitudinal axis A-A through a first through-bore 52 that extends through the gear thickness 44. In an embodiment the shank 32 has a diameter 54 that is oriented about perpendicular to longitudinal axis A-A. In a preferred embodiment, the diameter 54 of the shank 32 ranges from about 0.5 cm to about 5 cm. In addition, the shank 32 may comprise a lumen 56 that extends along longitudinal axis A-A through a length 58 of the shank 32. In a preferred embodiment, the lumen 56 is constructed having a lumen diameter that ranges from about 0.1 cm to about 2 cm. The lumen 56 is preferably constructed so that a guide wire (not shown) can extend therethrough.

In a preferred embodiment, the plate 38 comprises a plate thickness 60 that extends between opposed proximal and distal plate surfaces 62, 64. A second through-bore 66 extends through the thickness 60 of the plate 38 along longitudinal axis A-A. As illustrated, in FIGS. 1, 3, and 6, the distal end 42 of the shank 32 is positioned through the second through-bore 66 of the plate 38 so that the second surface 50 of the disc-shaped gear 34 faces the proximal surface 62 of the plate 38. In addition, the distal end 42 of the shank 32 extends past a housing edge 68 that resides at a distal end 67 of the distal housing portion 22. In a preferred embodiment, the distal edge 68 of the housing 18 defines an opening 70 at the distal end 67 of the housing that extends to the interior 24 of the distal housing portion 22. In a preferred embodiment, the housing opening 70 is dimensioned to allow for the mechanism 16 to be received therewithin.

Figure 6:
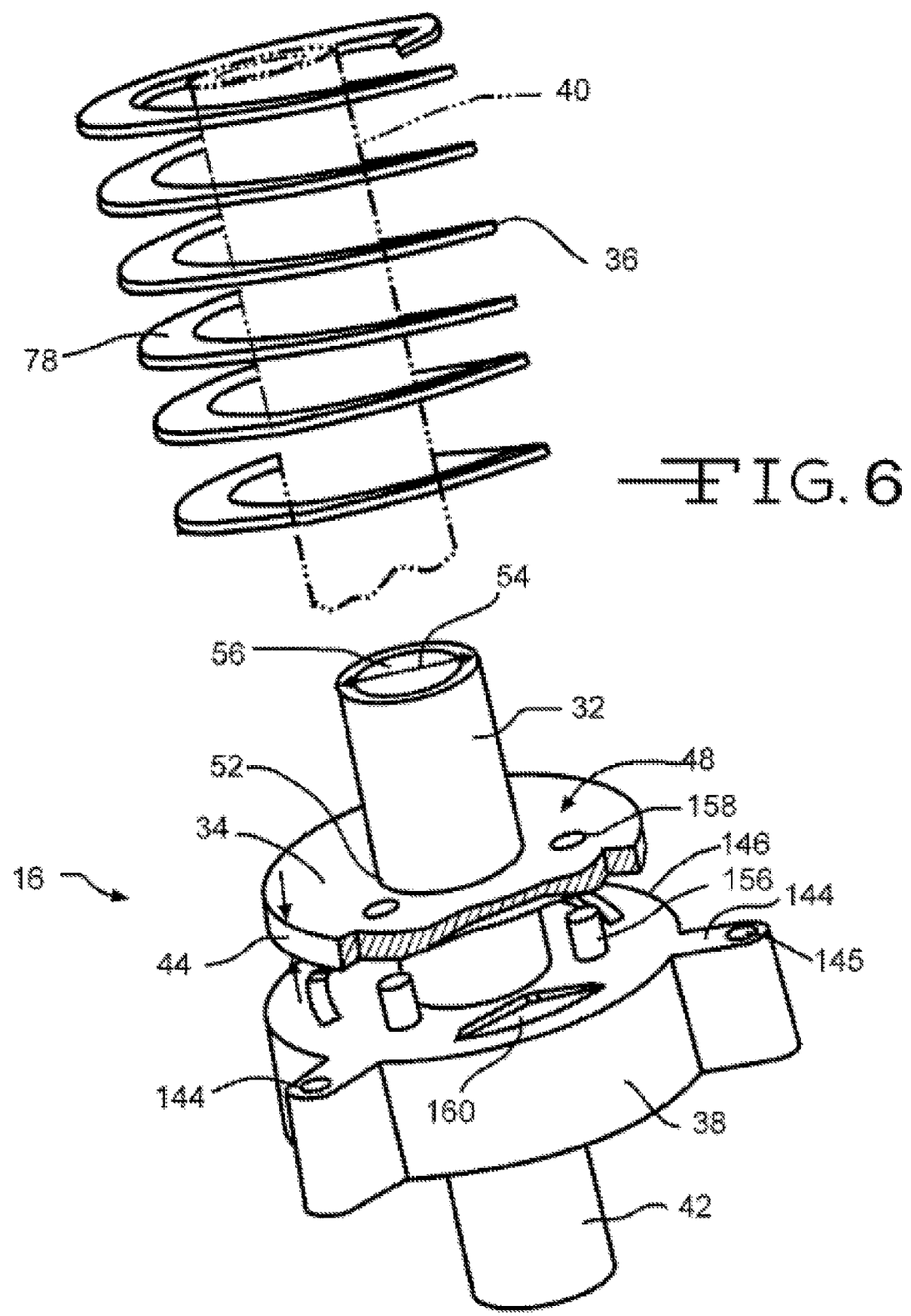
FIG. 6 shows a partially broken perspective view of the assembly of the mechanism of the torque limiting tool of the present invention.

As illustrated in FIG. 3, the plate 38 is fixedly secured at the distal end 67 of the housing 18. More specifically, the plate 38 is fixedly secured so that the plate thickness 60 at least partially resides within the opening 70 at the distal end 67 of the housing 18. The plate 38 may be positioned so that its distal surface 64 is positioned proximal, distal, or flush with the housing edge 68 at the housing opening 70. As illustrated in FIGS. 2 and 6, the plate 38 has a cross-section that is oriented about perpendicular to its thickness with a curved geometry. In a preferred embodiment, the plate 38 is constructed with a cross-section having a circular geometry. Nonetheless, the geometry of the cross-section of the plate 38 may be of a non-limiting polygon shape. Non-limiting examples of cross-section geometries may include, but are not limited to, a triangle, a pentagon or an octagon. As such, the housing opening 70 at the distal end 67 of the housing 18 is constructed of a geometry that allows for the plate 38 to be received therewithin.

The biasing member 36, having opposed first and second bias member ends 72, 74, is preferably positioned about the circumference of the shank 32. In a preferred embodiment, the biasing member 36 is positioned circumferentially around the proximal end 40 of the shank 32 so that its second end 74 biases against the first surface 48 of the gear 34 and its first end 72 facing the proximal end 12 biases against an interior housing proximal surface 76 at the proximal end of the housing interior 24. The biasing member 36 may comprise a spring 78 or a plurality of washers (not shown) such as a plurality of Bellville washers. The biasing member 36 provides a bias force in a distal direction against the first surface 48 of the gear 34. In a preferred embodiment, the biasing force encourages the mating of the gear 34 with the plate 38. The bias force can be modified through the use of springs having different spring tensions or by adjusting the number of washers. In addition, the bias force may be adjusted through the selection of the material with which the spring or Bellville washers are composed. For example, springs or washers composed of materials having a greater mechanical modulus of elasticity generally provide an increased bias force in comparison to springs and washers that are composed of materials of a lesser mechanical modulus of elasticity.

As illustrated in FIGS. 1, 2, and 3, the proximal portion 20 of the tool housing 18 comprises the driver end 26 with the keyed interface 28 (FIG. 1A). In a preferred embodiment, the keyed interface 28 of the driver end 26 is designed to engage with a device such as a motor that is capable of applying torque so that the housing 18 and the plate 38 rotate about longitudinal axis A-A.

FIG. 1A illustrates a magnified view of an embodiment of the keyed driver end 26. In a preferred embodiment, the keyed interface 28 of the driver end 26 may be constructed of a plurality of non-limiting configurations so that it is capable of being removably engaged with a corresponding receptacle of a motor (not shown) having a similar keyed configuration. In a preferred embodiment, the keyed interface 28 may be constructed of a plurality of unlimited geometries, examples of which may include, but are not limited to, a slotted end, a Phillips® end, a Torx® end, a clutch end, or a Pozidriv® end. In addition, the driver end 26 may be constructed having a driver end lumen 80 that extends along longitudinal axis A-A through the length of the driver end 26. Similar to the lumen 56 that extends through the shank 32, the driver end lumen 80 is dimensioned to allow for the passage of a guide wire (not shown). In a preferred embodiment, the shank lumen 56 aligns with the driver end lumen 80 along the rotational axis.

As illustrated in FIGS. 1 and 3, the driver end 26 extends in a proximal direction from a proximal end 82 of the distal housing portion 22. In a preferred embodiment, the keyed interface 28 of the driver end 26 comprises a shank 84 that extends from a driver end pedestal 86 (FIG. 1A) having a first pedestal portion 88 that extends to a second pedestal portion 90. As shown, the first pedestal portion 88 comprises an annular sidewall 92 that outwardly extends from the proximal end 82 of the distal housing portion 22.

As shown, the second pedestal portion 90 extends in a proximal direction from the first pedestal portion 88. In a preferred embodiment, the second pedestal portion 90 comprises opposed first and second sidewalls 94, 96 that meet and join opposed third and fourth second pedestal sidewalls 98, 100. As illustrated, the opposed first and second sidewalls 94, 96 are positioned about perpendicular to the opposed third and fourth sidewalls 98, 100. In an embodiment, either of the first, second, third or fourth sidewalls 94, 96, 98, 100 may have a planar or curved sidewall surface.

As illustrated in FIG. 1A, the shank 84 extends along longitudinal axis A-A from a first shank end 102 to a second shank end 104 in a proximal direction from a proximal end 106 of the second pedestal portion 90. In an embodiment the shank 84 may comprise a cross-section of a hexagon geometry that is oriented about perpendicular to longitudinal axis A-A. In the embodiment shown, the shank 84 comprises a cross-section oriented about perpendicular to longitudinal axis A-A having a hexagon shape. As illustrated, the shank 84 is constructed with a plurality of sidewall surfaces 108 that extend lengthwise about longitudinal axis A-A. Each of the sidewall surfaces 108 is preferably planar. Alternatively, the shank 84 may be constructed having a plurality of sidewall surfaces 108 that are curved.

In addition, the shank 84 may be constructed having a recess band 112 that extends circumferentially around longitudinal axis A-A. As illustrated, the recess band 112 comprises a recess band surface 114 that at least partially extends within the shank 84. As illustrated, the recess band 112 has a band width 116 that extends parallel to longitudinal axis A-A. In a preferred embodiment, the recess band 112 may be designed having a curved surface 114 that extends inward towards the longitudinal axis A-A. The recess band 112 serves to provide a surface on which a motor or other tool can attach and detach.

As shown in FIG. 3, the torque limiting mechanism 16 resides within the housing interior 24 at the distal end portion 22 of the housing 18. As illustrated, the interior 24 extends within the housing 18 from the opening 70 at the distal housing edge 68 to an end sidewall 118 that resides at the proximal end 82 of the distal housing portion 22. In a preferred embodiment, the housing interior 24 is defined by a housing sidewall 120 that extends distally from the end wall 118 at the proximal end 82 of the distal housing portion 22 to the distal housing opening 70. In a preferred embodiment, the end wall 118 extends radially about longitudinal axis A-A. As illustrated, the end wall 118 circumferentially extends around the rotational axis thereby providing an annular shoulder. As illustrated in FIGS. 1 and 3, the driver end 26 of the proximal housing portion 20 extends in a proximal direction along longitudinal axis A-A from the exterior shoulder surface 126 of the proximal end wall 118.

As illustrated in FIG. 3, the second end 74 of the biasing member 36 is positioned within the housing interior 24 so that it biases against an interior surface 128 of the proximal end wall 118. In a preferred embodiment, the interior surface 128 of the end wall 118 is oriented about perpendicular to longitudinal axis A-A.

As illustrated in FIGS. 1 and 3, the distal housing sidewall 120 extends from the proximal end wall 118 to the distal end housing opening 70 at the edge 68 of the housing distal end 67. In a preferred embodiment, the distal housing sidewall 120 defines the boundaries of the interior 24 of the housing distal portion 22 within which the mechanism 16 resides.

As illustrated in FIG. 3, the interior housing region 24 is dimensioned to receive the gear 34 and the biasing member 36 of the mechanism 16. In a preferred embodiment, the distal housing sidewall 120 forms a cylindrically shaped interior 24 within which the mechanism 16 is received. In a preferred embodiment, the interior 24 has a diameter oriented perpendicular to the rotational axis formed by the distal housing sidewall 120 that ranges from about 0.5 cm to about 5 cm. In addition, the interior 24 has a length that extends along the rotational axis from about 2 cm to about 10 cm. As shown, the annular sidewall 120 also defines the distal housing end opening 70. As illustrated, the distal end 130 of the distal housing sidewall 120 forms the edge 68 at the distal end 67 of the housing 18. In a preferred embodiment, the opening 70 at the housing edge 68 has a diameter 132 that ranges from about 0.1 cm to about 5 cm.

As illustrated in FIG. 3, a channel 134 extending from a first channel opening 136 to a second channel opening 138 connects the housing interior 24 to the driver end lumen 80. As shown, the first end 136 of the channel 134 extends through the end sidewall 118. The second channel opening 138 is connected to the driver end lumen 80 opening. The channel 134 extends part way through the thickness of the driver end 26 towards the proximal end 20 of the housing 18 along longitudinal axis A-A. In a preferred embodiment, the channel 134 is constructed having an opening that is dimensioned to receive the proximal end 40 of the shank 32. The proximal end 40 of the shank 32 is designed to rotate freely about rotational axis A-A within the channel 134. The channel 134 preferably provides mechanical stability to the proximal end 40 of the shank 32 and ensures that the shank 32 rotates about rotational axis A-A. In addition, the channel 134 may provide for axial movement of the shank 32 therewithin. The housing 18 may be constructed with a channel transition 140 that connects the second opening 138 of the channel 134 to the distal end of the driver end lumen 80. As illustrated in FIG. 3, the transition 140 is preferably constructed having a frusto-conical shape. Alternatively, the housing 18 could be constructed without the channel 134 and/or the transition portion 140. In this case, the proximal end 40 of the shank 32 would be positioned at or a distance distal of the interior surface 128 of the wall 118.

As illustrated in FIGS. 2 and 3, the plate 38 is secured at least partially within the distal end 67 of the housing 18. In a preferred embodiment, the plate 38 is positioned within the distal end opening 70 of the housing 18 so that at least a portion of the thickness 60 of the plate 38 extends proximal of the housing distal edge 68. As shown, a plurality of fasteners 142 secures the plate 38 within the distal end 22 of the housing 18. In a preferred embodiment, the plate 38 comprises at least one spoke 144 (FIG. 4) that outwardly extends from a hub 146 of the plate 36. In an embodiment, each spoke 144 comprises a finger member that radially extends from an origin located at the rotational axis. The at least one plate spoke 144 is received within a respective housing projection 148 (FIG. 2) that forms an enclosure 150 for the plate spoke 144. As illustrated, the housing projection 148 comprises an inlet 152 (FIG. 1) within which the plate spoke 144 is received and anchored therewithin. Each projection 148 is preferably formed by the distal housing sidewall 120. In a preferred embodiment, each projection 148 is a continuation of the distal housing sidewall 120. The housing fastener 142 may be positioned through an opening 145 that extends through a proximal end 154 of the projection 148. That way, the fasteners 142 secure the plate spoke 144 within the housing distal end 22 to thereby prevent movement of the plate 38 with respect to the housing 18 and the gear 34. Alternatively, the plate 38 may be constructed without a spoke 144. In this embodiment, the plate 38 may be secured within the opening 70 at the distal housing end 67 with the use of an adhesive or by welding the plate 38 therewithin.

In an embodiment, the plate 38 of the mechanism 16 comprises at least one post 156 (FIG. 2) that outwardly extends from its proximal surface 62. The at least one post 156 extends through and engages with a corresponding third through-bore 158 that extends through the thickness 44 of the gear 34. Alternatively, the at least one post 156 may be positioned within an opening that at least partially extends through the thickness 44 of the gear 34. As illustrated, three posts 156 are shown that outwardly extend from the proximal surface 62 of the plate 38. Each of the posts 156 engage with the third through-bore 158 that extends through the gear 34. This post and through-bore engagement provides for the first stage or mode of the torque limiting mechanism 16.

In addition to the post 156, the plate 38 of the mechanism 16 is constructed having at least one raised tooth or ridge 160 (FIG. 4) that outwardly extends from the proximal surface 62 thereof. In a preferred embodiment, the raised tooth 160 engages with a corresponding recess 162 (FIG. 5) that at least partially resides within the thickness 44 of the gear 34. The engagement of the tooth 160 with the recess 162 provides for the second torque limiting stage or mode of the mechanism 16. Thus, when either or both of the posts 156 or the raised tooth 160 of the plate 38 is engaged with the gear 34, rotational movement of the drive end 26 of the housing 18 imparts rotational movement or torque to the stationary plate 38 which, in turn, rotates the gear 34 and connectable drive shaft 30 about axis A-A. While it is preferred that the post 156 and tooth 160 outwardly extend from the proximal sidewall surface 62 of the plate 38, it is contemplated that the post 156 and/or the tooth 160 may outwardly extend from the distal sidewall surface 64. Likewise, it is contemplated that the recess 162 may extend through either of the first or second sidewall surfaces 48, 50 of the gear 34. In either case, the mechanism 16 is constructed so that the tooth 160 and the recess 162 are positioned in opposition to each other.

As shown in FIGS. 4, 4A, 6, 7, and 7A-7C, the least one tooth 160 outwardly extends from the proximal surface 62 of the plate 38. In a preferred embodiment, the tooth 160 extends lengthwise from a first tooth end 164 to a second tooth end 166. In a preferred embodiment, each tooth 160 is constructed with a first ramp 168 having a first ramp surface 170 and a second ramp 172 having a second ramp surface 174 that meet at a raised plateau 176 having a plateau surface 178 that extends therebetween. In a preferred embodiment, the first ramp 168 extends in an upwardly direction from a first ramp base 180 at the proximal surface 62 of the plate 38 to a first ramp peak 182 that meets the raised plateau 176. In a preferred embodiment illustrated in FIG. 7, the first ramp 168 is oriented at a first ramp angle 184 that ranges from about 5° to about 75°. The first ramp angle 184 is defined as an angle that extends between an imaginary line B-B that extends along the proximal surface 62 of the plate 38 and an imaginary line C-C that extends along the first ramp surface 170 of the first ramp 168. The second ramp 172 extends in an upwardly direction from a second ramp base 186 at the proximal surface 62 of the plate 38 to a second ramp peak 188 that meets the plateau 176. In a preferred embodiment, the second ramp surface 174 is oriented at a second ramp angle 190 that ranges from about 5° to about 75°. The second ramp angle 190 is defined as an angle that extends between the imaginary line B-B that extends along the proximal surface 62 of the plate 38 and an imaginary line D-D that extends along the second ramp surface 174.

In a preferred embodiment, the first and second ramps 168, 172 are positioned facing each other. More specifically, the first and second ramp peaks are positioned in opposition to each other. As illustrated, the first and second peaks 182, 188 of the respective first and second ramps 168, 172 may meet at the plateau 176 that is positioned and extends therebetween. In a preferred embodiment, the plateau 176 may have a length that spans from about 1 mm to about 10 mm between the respective first and second ramps 168, 172. The plateau 176 may be positioned at a plateau height that ranges from about 0.1 cm to about 5 cm. The plateau height is measured between imaginary line B-B, which extends along the proximal plate surface 62, to the plateau surface 178. In addition, each tooth 160 has a height that extends from the proximal plate surface 62 to the plateau 176. In a preferred embodiment, the tooth height may range from about 0.1 cm to about 3 cm. The teeth 160 that extend from the plate surface 62 may have a similar height or alternatively may be of different heights. The tooth height may be adjusted to modify the friction between the corresponding ramped teeth 160 and recess 162. Alternatively, the first and second peaks 182, 188 of the first and second ramps 168, 172 may meet at a point, in which case the plateau 176 would not exist.

In an embodiment, the tooth 160 comprising the plateau 176 and first and second ramps 168, 172 ride within the recess 162 that extends at least partially within the thickness 44 of the gear 34. More specifically, the first and second surfaces 170, 174 of the first and second ramps 168, 172, in addition to the plateau 176, ride within the recess 162 that is positioned part-way within the thickness of the second surface 50 of the gear 34.

FIG. 5A illustrates a magnified view of an embodiment of the recess 162 that at least partially resides within the thickness 44 of the gear 34. In an embodiment, each recess 162 comprises first and second recess surfaces 192, 194 that respectively extend from the second surface 50 of the gear 34 and meet at a recess dwell surface 196.

As shown in FIGS. 5 and 5A, the first recess surface 192 extends at a downward angle from the second surface 50 of the gear 34 at a first recess surface top end 198 to a first recess surface bottom end 200 that meets with the dwell surface 196. The second recess surface 194 extends in a downward angle from the second surface 50 at a second recess surface top end 202 to a second recess surface bottom end 204 that meets with the dwell surface 196 of the recess 162. In a preferred embodiment shown in FIG. 7A, the first recess surface 192 is oriented at a first recess surface angle 206 that ranges from about 5° to about 75°. The first recess surface angle 206 is defined as an angle that extends between the imaginary line E-E that extends along the second surface 50 of the gear 34 and imaginary line F-F that extends along the first recess surface 192. The second recess surface 194 is oriented at a second recess surface angle 208 that ranges from about 5° to about 75°. The second recess surface angle 208 is defined as an angle that extends between an imaginary line E-E that extends along the proximal surface 50 of the gear 34 and an imaginary line G-G that extends along the second recess surface 194. It is noted that the angular measurements for the recess surface angles and the ramp surface angles are in absolute values to account for different measurement orientations. The recess dwell surface 196 resides at least partially within the thickness 44 of the gear 34 and serves as a bridge between the first and second recess surfaces 192, 194. More specifically, the recess dwell surface 196 extends between the bottom ends 200, 204 of the first and second recess surfaces 192, 194. In a preferred embodiment, the dwell surface may have a length that ranges from about 0.1 cm to about 5 cm. In addition, the dwell surface 196 preferably extends about parallel to the second surface 50 of the gear 34.

While it is preferred that the post 156 and the tooth 160 which comprises at least one ramp 168, 172 are positioned so that they outwardly extend from the proximal surface 62 of the plate 38, it is contemplated that either or both of the post 156 and tooth 160 may outwardly extend from either of the first or second surfaces 48, 50 of the gear 34. Likewise, while it is preferred that the recess 162 and third through-bore 158 at least partially extend through the second surface 50 of the gear 34, it is contemplated that they may at least partially extend through either sidewall surface 62, 64 of the plate 38. In either case, the mechanism is constructed so that the at least one tooth 160, comprising at least one ramp 168, 172 is positioned facing the recess 162 regardless of whether the post 156 and tooth 160 extends from the sidewalls of the plate 38 or the gear 34 and whether the recess 162 extends at least partially within either of the sidewall surfaces of the plate 38 or gear 34.

As illustrated in FIG. 4, at least one tooth 160 is preferably positioned along the proximal surface 62 of the plate 38 between the second through bore 66 and an outer perimeter 210 of the plate 38. As illustrated, three teeth 160 are shown extending from the proximal surface 62 of the plate 38. In the embodiment shown, three teeth 160 are spaced apart at equal distances circumferentially about longitudinal axis A-A along the proximal surface 62 of the plate 38. In a preferred embodiment, each of the three teeth 160 is positioned at an equal radial distance from the plate outer perimeter 206 of the hub 146 of the plate 38. While a total of three teeth 160 are shown, the plate 38 may be constructed having one, two, or more teeth 160 that outwardly extend from either of the proximal or distal plate surfaces 62, 64.

In an embodiment, each of the plurality of teeth 160 may be positioned so that the lengths of the teeth 160 have a curved orientation with respect to the outer plate perimeter 146. More specifically, each of the teeth 160 may be positioned about the second through-bore 66 of the plate 38 so that the respective first and second ramps 168, 172 of the teeth 160 are oriented so that they are positioned along a first imaginary concentric circle having a focal point at longitudinal axis A-A.

In an embodiment, the first and second ramp surfaces 170, 174 of the tooth 160 are designed to ride along either of the first or second ramped recess surfaces 192, 194, respectively as the plate is rotated in either a clockwise or counterclockwise manner. In a preferred embodiment, application of a torque to the housing 18, in particular, the driver end 26, causes the plate 38 to rotate, which in turn, causes the gear 34 and shank 32 to rotate. As such, rotation of the plate 38 with respect to the gear 34 causes the teeth 160 to ride within their respective recess 162. In a preferred embodiment, continued application of torque to the drive end 26 of the housing 18 causes the first or second ramp surface 170, 174 of the teeth 160 to come into physical contact with either of the ramped first or second recess surfaces 192, 194. Once a torque threshold has been exceeded, the respective ramp surfaces 170, 174 of the teeth 160 overcome the bias force that mates the respective plate 38 and gear 34 together so that the teeth 160 ride out of the recess 162. For example, as torque is applied to the housing 18 in a clockwise manner, the first ramp surface 170 of the tooth 160 rides up the first recess surface 192 until the tooth 160 exits the recess 162. It is at this point that torque is no longer being transferred from the housing 18 to a connected drive shaft 30 by the mating teeth 160 and recess 162 mechanism. Likewise, when torque is applied to the housing 18 in a counterclockwise manner, the second ramp surface 174 of the tooth 160 rides up the second recess surface 194 until the tooth 160 exits its respective recess 162. Similarly to the example in which torque is applied in a clockwise manner, it is at this point when the tooth 160 exits its respective recess 162 that torque is no longer being applied to a connected drive shaft 30 by the engagement of the mating teeth 160 and recess 162.

As previously discussed, the plate 38 may comprise at least one post 156 that outwardly extends from the plate proximal surface 62. In a preferred embodiment, the at least one post 156 is oriented about perpendicular from the proximal surface 62 of the plate 38 therefrom. As illustrated in the embodiment shown in FIG. 4, the plate 38 comprises three posts 156, however, it is contemplated that there may be one, two or more posts 156 that outwardly extend from the plate surface 62. As shown in an embodiment, each of the posts 156 may be positioned between adjacent teeth 160. In an embodiment, each of the posts 156 may be positioned along a second imaginary concentric circle having a focal point at longitudinal axis A-A. In a preferred embodiment, each of the posts 156 are positioned between two adjacent teeth 160 oriented along the same imaginary concentric circle of the teeth 160 that resides along the proximal plate surface 62. It is noted that the first and second imaginary concentric circles may have diameters of the same or different size.

In an embodiment, when a torque is applied at the driver end 26 of the housing 18 that exceeds a pre-determined first torque threshold value, the applied torque causes the at least one post 156 to break and disengage from within the third through-bore 158 or opening. Once the at least one post 156 becomes disengaged from the gear 34, i.e., the first mechanism mode, the application of torque by the tool 10 becomes controlled by the engagement of the at least one tooth 160 residing within its recess 162, i.e., the second mechanism mode. In an embodiment, once a torque that exceeds the second torque threshold is applied by the housing 18 to the gear 34, the applied torque forces the at least one tooth 160 out of its corresponding recess 162. In a preferred embodiment, the mechanism 16 of the present invention is designed so that the first torque threshold is greater than the second torque threshold. Thus, the torque limiting mechanism 16 of the present invention is designed so that once the greater of the two torque limits has been exceeded, the torque limit of the tool is set to a second torque threshold limit of a lesser amount as established by the engagement of the at least one tooth 160 and recess 162. In other words, once the greater of the torque threshold limits has been exceeded, the force of the applied torque causes the at least one post 156 to break and thus disengage the post 156 from its corresponding third through-bore 158. The torque limit is then established by mating engagement of the at least one tooth 160 within a corresponding recess 162 that extends at least partially within the thickness 44 of the gear 34.

Figure 7:
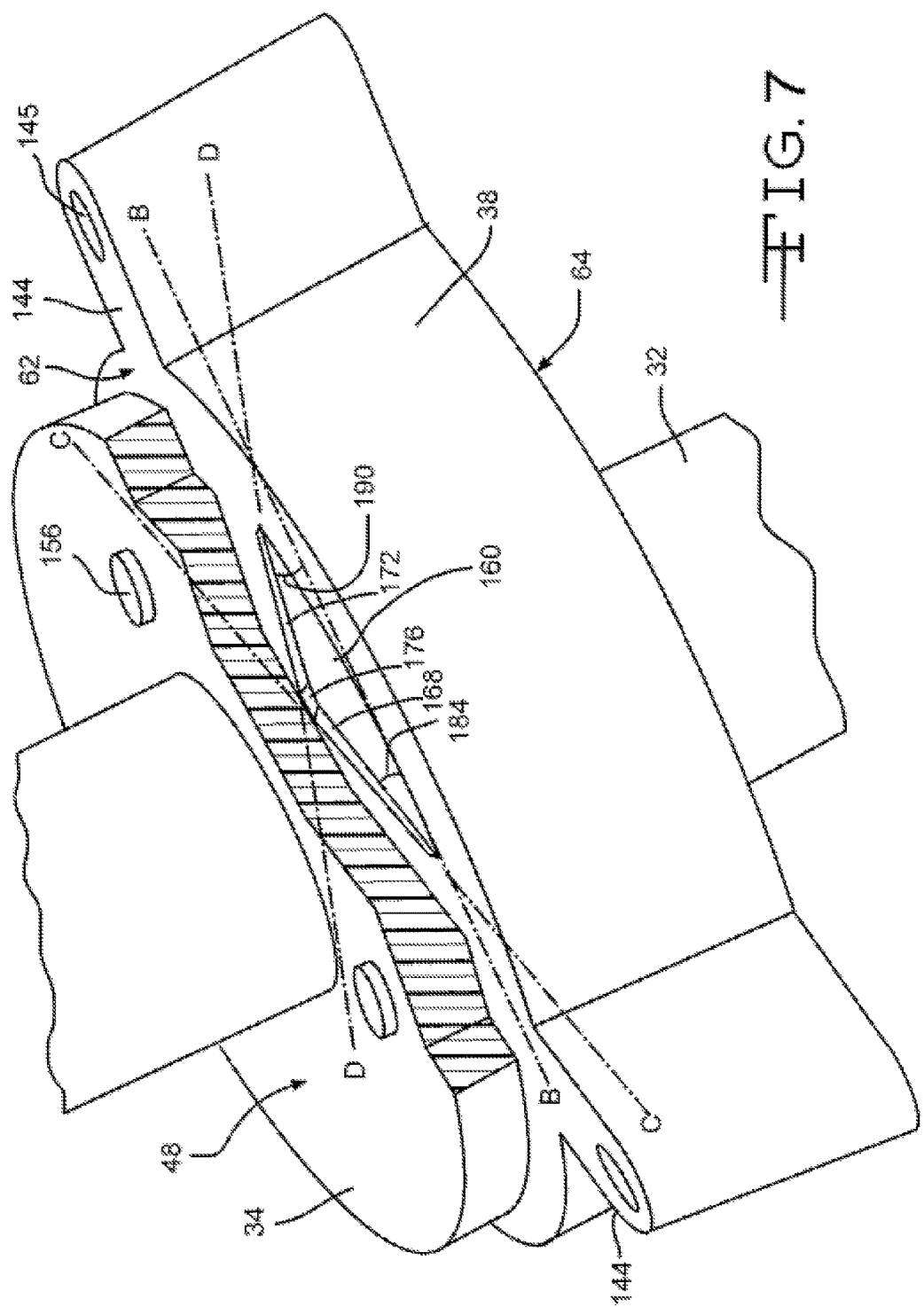
FIG. 7 shows a magnified partially broken perspective view of the plate engaged with the gear of the torque limiting mechanism of the present invention.

FIGS. 7, 7A, 7B, and 7C illustrate an embodiment of the sequence of events in which torque is applied to the two-stage torque limiting mechanism 16 of the present invention. FIG. 7 is a partially broken perspective view that illustrates an embodiment of the first-stage configuration of the mechanism 16. As shown, the posts 156 and teeth 160 are engaged within their respective through-bore openings 158 and recesses 162 of the gear 34. As illustrated, the tooth 160 is mated within its respective recess 162 as the surface 178 of the plateau 176 of the tooth 160 is positioned in contact with the dwell surface 196 of the recess 162. In addition, the posts 156 are received within their respective through-bore openings 158 that extend through the gear 34. It is at this first stage position that a maximum amount of torque can be transferred from the housing 18 and plate 38 to the shank 32 of the gear 34.

Figure 7C:
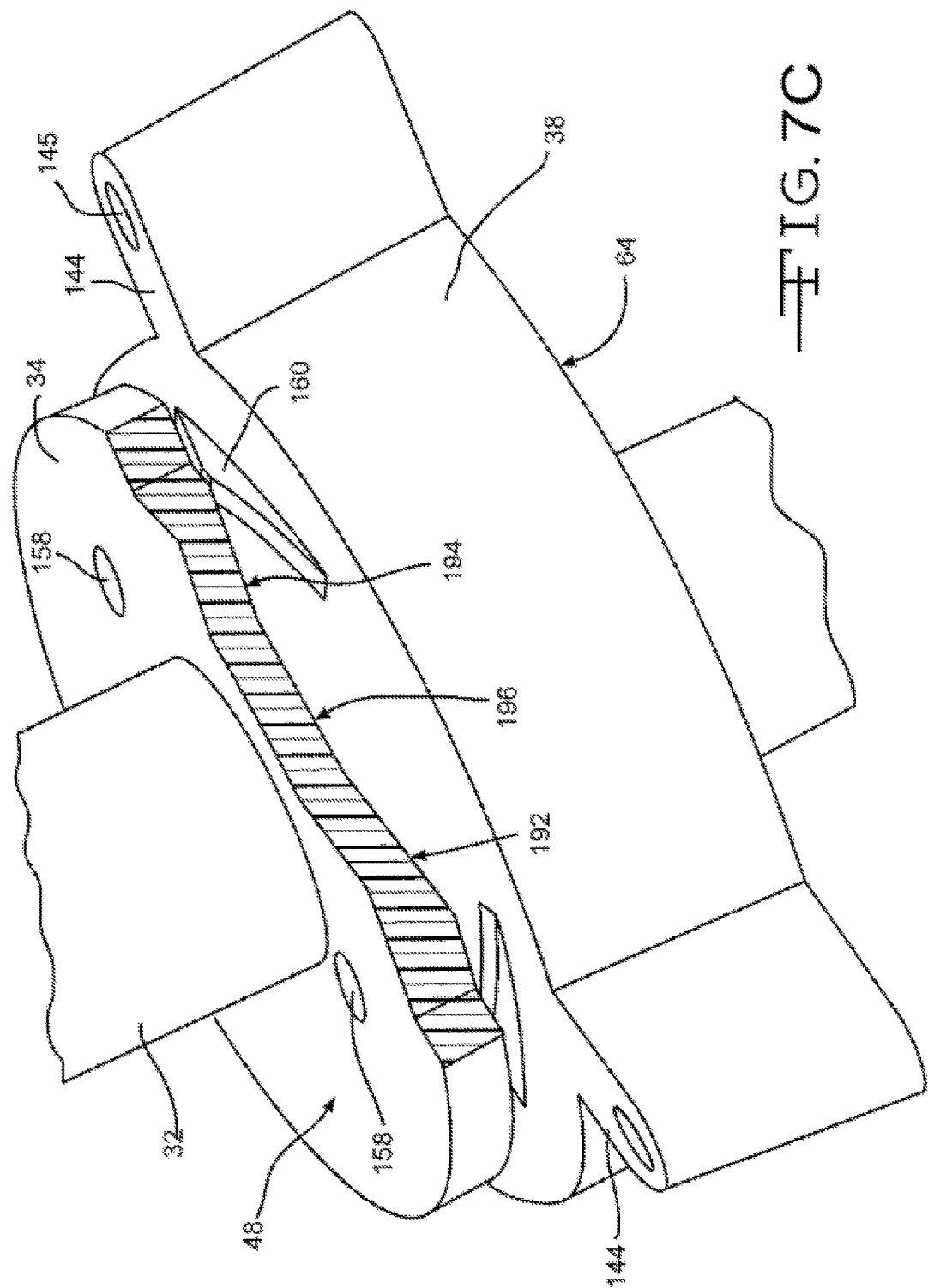

FIG. 7A illustrates an embodiment in which the first torque threshold has been exceeded as the housing 18 is rotated in a clockwise rotation. As illustrated the posts 156 have been broken or sheered off and are disengaged from their respective through-bore openings 158. As illustrated, the mechanism 16 has been modified as the posts 156 have been removed from their respective through-bore openings 158. The mechanism 16 is now configured in the second stage in which the application of torque is limited by the mating of the teeth 160 within the recesses 162. As shown, the second ramp surface 174 of the tooth 160 is in contact with the second recess surface 194. FIG. 7B illustrates an embodiment in which a torque exceeding a second torque limit is further being applied to the housing 18 in a counterclockwise direction. As shown, the second recess surface 194 is illustrated to be further riding up the second ramp surface 174 of the tooth 160. FIG. 7C illustrates an embodiment in which the tooth 160 has exited the recess 162. As illustrated, the plateau 176 is shown to be in physical contact with the second surface 50 of the gear 34. It is at this point that the maximum second torque limit threshold has been reached as the force of the applied torque has caused the tooth 160 to exit the recess 162.

In an embodiment, the limits of the first and second torque limit thresholds can be modified by adjusting the number of respective post 156 and through-bore 158 pairs as well as the number of tooth 160 and recess 162 pairs. In addition, the first and second torque limit thresholds can be adjusted by modifying the diameter of the posts 156 and through-bores 158. Likewise, the torque limits can be adjusted by modifying the angles of the respective ramped surfaces of the teeth 160 and recesses 162 or by adjusting the strength of the bias force that is exerted by the biasing member 36. In general, the first and second torque limit thresholds can be increased by increasing the amount of friction between the mated plate 38 and gear 34. Likewise, the torque limit thresholds can be reduced by minimizing the friction between the plate 38 and gear 34.

Furthermore, the respective first and second torque threshold limits may also be adjusted by constructing the torque limiting mechanism 16 of different materials having different modulus of elasticities. For example, constructing the torque limiting mechanism 16 from materials having a greater modulus of elasticity generally increases the torque limit. In contrast, constructing the torque limiting mechanism 16 from materials having a lesser modulus of elasticity, generally decreases these torque threshold limit. Non-limiting examples of materials that have a relatively "low" modulus of elasticity may include, but are not limited to, rubber and low density polyethylene having modulus of elasticity's ranging from about 0.01 GPa to about 1.0 GPa. Non-limiting examples of materials having a relatively "medium" modulus of elasticity may include, but are not limited to, polypropylene, polyethylene terephthalate (PET), nylon and polystyrene having a modulus of elasticity ranging from about 1.0 GPa to about 4.0 GPa. Non-limiting examples of relatively "high" modulus of elasticity generally comprise those materials having a modulus of elasticity greater than 4.0 GPa. As defined herein modulus of elasticity is a mechanical property of linear elastic solid materials. Modulus of elasticity is the force (per unit area) that is required to stretch (or compress) a material sample. In a preferred embodiment, the torque limiting tool can be design to apply a maximum torque from about 0.007 N-m (1 oz. per in) to about 122 N-m (90 lbf).

In a preferred embodiment the housing 18 may be composed of a polymeric material. In addition, the plate 38 and/or gear 34 may be composed of a polymeric material. Such materials may include but are not limited to thermoplastics such as acrylics, acrylonitrile butadiene styrene (ABS), poly(hexamethylene adipamide), polylactic acid, polybenzimidazole, polycarbonate, polyether sulfone, poly ether ether ketone (PEEK), polyetherimide, polyethylene, polyphenylene oxide, polyphenylene sulfide, polypropylene, polystyrene, polyvinyl chloride, and combinations thereof. Such polymeric materials provide a durable structure and allow for flexure of the teeth 160 and/or posts 156. Alternatively, the housing 18 and/or the plate 38 and gear 34 may be constructed of a metallic material such as various stainless steel alloys, a ceramic material, such as a stainless steel alloy, or combinations thereof.

While the preferred embodiments of the torque limiting tool and methods have been described in reference to the environment in which they were developed, they are merely illustrative of the principles of the inventions. Other embodiments and configurations may be devised without departing from the spirit of the inventions and the scope of the appended claims.

Thus, it can be seen that the present invention provides a torque limiting tool and mechanism thereof that is designed to limit the application of torque at two different threshold amounts. The torque limiting tool is constructed having a plate and gear with respective teeth, posts, recesses and through-bores that physically engage each other. The amount of torque applied by the tool can be engineered based on the diameter of the post and angle of the respective ramped surfaces of the mated teeth and recesses. In addition, the amount of torque applied by the tool can be adjusted by modifying the tension provided by the bias member or constructing the gear or plate of different materials.

What is claimed is:
1. A torque limiting tool, comprising:
a) a housing having spaced proximal and distal housing portions that extend along a rotational axis;
b) a torque limiting mechanism disposed within the housing, the torque limiting mechanism comprising:
  i) a plate having a plate thickness and a first through-bore extending therethrough, wherein at least a portion of the plate thickness is secured within the housing;
  ii) a gear positioned opposed from the plate having a gear thickness with a second through-bore extending therethrough;
  iii) a shank having a shank proximal end that extends to a shank distal end along the rotational axis, the shank distal end positioned through the first through-bore and the shank proximal end positioned through the second through-bore, wherein the shank is secured to the gear or the plate;
  iv) a first ramp having a first ramp surface and a post spaced from the first ramp, the post and first ramp extending outwardly from a first sidewall surface of the gear or the plate;
  v) a recess dimensioned to receive the first ramp and an opening spaced from the recess, the recess and opening positioned at least part-way through the thickness of the other of the plate or gear that comprises the first ramp and post;
  vi) a bias member having opposed first and second bias member ends positioned circumferentially around the shank, wherein the first member end is positioned adjacent the plate or the gear and the second bias member end positioned adjacent an interior housing surface so that a biasing force is capable of being generated towards the plate or the gear; and c) wherein the plate and gear are positioned so that the first ramp faces the recess and wherein application of a torque at the proximal housing portion causes the post to engage within the opening and the ramp to engage within the recess thereby causing the shank to rotate about the rotational axis.

2. The torque limiting tool of claim 1 wherein the first ramp surface extends outwardly from the first sidewall surface of the plate or the gear at a first ramp angle to a plateau having a plateau surface.

3. The torque limiting tool of claim 2 wherein the first ramp angle is measured between the first sidewall surface of the plate or the gear and the first ramp surface, wherein the first ramp angle has an absolute value that ranges from about 5° to about 75°.

4. The torque limiting tool of claim 2 wherein the plateau has a plateau height that extends from the first sidewall surface of the plate or gear to the plateau surface, wherein the plateau height ranges from about 0.5 cm to about 5 cm.

5. The torque limiting tool of claim 1 wherein a second ramp having a second ramp surface extends outwardly from the first sidewall surface of the plate or gear and meets the first ramp at the plateau.

6. The torque limiting tool of claim 1 wherein the recess comprises a first recess surface that extends at a first recess surface angle from a second sidewall surface of the plate or the gear to a recess dwell surface that resides part-way within the thickness of the plate or the gear.

7. The torque limiting tool of claim 6 wherein the first recess surface angle is measured between the second sidewall surface and the first recess surface, wherein the first recess surface angle has an absolute value that ranges from about 5° to about 75°.

8. The torque limiting tool of claim 1 wherein the proximal housing portion comprises a driver end having a keyed interface.

9. The torque limiting tool of claim 1 wherein the bias member comprises a spring or a plurality of washers.

10. The torque limiting tool of claim 1 wherein the plate comprises at least one spoke that outwardly extends from a hub of the plate.

11. The torque limiting tool of claim 10 wherein the distal housing portion comprises at least one housing projection formed by a distal housing sidewall that extends outwardly at a distal housing end, wherein the projection forms an enclosure dimensioned to receive the plate spoke.

12. The torque limiting tool of claim 1 wherein at least one of the plate, the shank and the gear are composed of a polymeric material or a metallic material.

13. The torque limiting tool of claim 1 wherein the plate or the gear is composed of a material having a modulus of elasticity ranging from about 0.01 GPa to about 10 GPa.

14. A torque limiting tool, comprising:
a) a housing having spaced proximal and distal housing portions that extend along a rotational axis;
b) a torque limiting mechanism disposed within the housing, the torque limiting mechanism comprising:
 i) a plate having a first plate through-bore that extends through a plate thickness, a post spaced from a tooth comprising at least a first ramp, wherein the post and tooth extend outwardly from a plate sidewall surface;
 ii) a gear positioned opposed from the plate having spaced apart second and third gear through-bores that extend through a gear thickness and a recess dimensioned to receive the tooth extending through a gear sidewall surface part-way through the gear thickness, wherein the tooth is oriented opposed from the recess;
 iii) a shank having a shank proximal end that extends to a shank distal end along the rotational axis, the shank distal end positioned through the plate first through-bore and the shank proximal end positioned through the second gear through-bore, the shank secured to the gear;
 iv) a bias member having spaced apart first and second bias member ends positioned circumferentially around the shaft proximal of the gear and plate, wherein the first bias member end is contactable to a gear sidewall surface and the second bias end is contactable to an interior housing surface so that a biasing force is generated towards the gear and plate; and
c) wherein application of a torque at the proximal housing portion causes the post to engage within the third gear through-bore and the tooth to engage within the recess thereby causing the shank to rotate about the rotational axis.

15. The torque limiting tool of claim 14 wherein the first ramp of the tooth has a first ramp surface that extends outwardly from the plate sidewall surface at a first ramp angle to a plateau having a plateau surface.

16. The torque limiting tool of claim 15 wherein the first ramp angle is measured between the plate sidewall surface and the first ramp surface, wherein the first ramp angle has an absolute value that ranges from about 5° to about 75°.

17. The torque limiting tool of claim 15 wherein the plateau has a plateau height extending from the plate sidewall surface to the plateau surface, wherein the plateau height ranges from about 0.5 cm to about 5 cm.

18. The torque limiting tool of claim 15 wherein the plateau surface extends parallel to the plate sidewall surface.

19. The torque limiting tool of claim 14 wherein the at least one tooth comprises a second ramp with a second ramp surface that extends outwardly from the plate sidewall surface that meets the plateau.

20. The torque limiting tool of claim 14 wherein the recess comprises a first recess surface that extends at a first recess surface angle from the gear sidewall surface to a recess dwell surface that resides part-way in the gear thickness.

21. The torque limiting tool of claim 20 wherein the first recess surface angle is measured between the gear sidewall surface and the first recess surface, wherein the first recess surface angle has an absolute value that ranges from about 5° to about 75°.

22. The torque limiting tool of claim 14 wherein the proximal housing portion comprises a driver end having a keyed interface.

23. The torque limiting tool of claim 14 wherein the bias member comprises a spring or a plurality of washers.

24. The torque limiting tool of claim 14 wherein the plate comprises at least one spoke that outwardly extends from a hub of the plate.

25. The torque limiting tool of claim 24 wherein the distal housing portion comprises at least one housing projection formed by a distal housing sidewall that outwardly extends at a distal housing end, wherein the projection forms an enclosure dimensioned to receive the plate spoke.

26. The torque limiting tool of claim 14 wherein at least one of the plate, the shank and the gear are composed of a polymeric material or a metallic material.

27. The torque limiting tool of claim 14 wherein application of a torque that exceeds a first torque limit causes the post to disengage from the third gear through-bore.

28. The torque limiting tool of claim 14 wherein the plate or the gear is composed of a material having a modulus of elasticity ranging from about 0.01 GPa to about 10 GPa.

29. A torque limiting mechanism, comprising:
  a) a plate having a plate sidewall surface and a first through-bore that extends through a plate thickness, a post that extends outwardly from the plate sidewall surface spaced from a first ramp having a first ramp surface that extends outwardly from the plate sidewall surface at a first ramp angle;
  b) a gear having a gear thickness with a second through-bore extending through the gear thickness, at least one recess dimensioned to receive the at least one ramp spaced from an opening, the recess and opening extend part-way through the gear thickness, wherein the gear is oriented opposed from the plate so that the at least one recess faces the ramp and post;
  c) a shank having a shank proximal end that extends to a shank distal end along a rotational axis, the shank distal end positioned through the plate first through-bore and the shank proximal end positioned through the gear second through-bore, the shank secured to the gear;
  d) a bias member positioned circumferentially around the shank proximal the gear and plate, wherein the biasing member is capable of generating a biasing force towards the plate or the gear; and
  e) wherein application of a torque at the plate causes the post to engage within the gear opening and the ramp to engage within the recess thereby causing the shank to rotate about the rotational axis.

30. The torque limiting mechanism of claim 29 wherein the first ramp angle extends outwardly from the plate sidewall surface to a plateau having a plateau surface.

31. The torque limiting mechanism of claim 30 wherein the first ramp angle is measured between the plate sidewall surface and the first ramp surface, wherein the first ramp angle has an absolute value that ranges from about 5° to about 75°.

32. The torque limiting mechanism of claim 30 wherein the recess comprises at least one recess surface that extends at a first recess surface angle through the sidewall gear surface to a recess dwell surface that resides part-way into the gear thickness.

33. The torque limiting tool of claim 32 wherein the first recess surface angle is measured between the gear surface and the first recess surface, wherein the first recess surface angle has an absolute value that ranges from about 5° to about 75°.

34. The torque limiting tool of claim 30 wherein at least one of the plate, the shank and the gear are composed of a polymeric material or a metallic material.

35. The torque limiting tool of claim 30 wherein the plate or the gear is composed of a material having a modulus of elasticity ranging from about 0.01 GPa to about 10 GPa.

* * * * *